(12) United States Patent
Newton

(10) Patent No.: US 7,727,165 B2
(45) Date of Patent: Jun. 1, 2010

(54) PEAK FLOW MEASUREMENT DEVICE

(75) Inventor: Douglas Paul Newton, Bowburn (GB)

(73) Assignee: University of Newcastle-Upon-Tyne, Newcastle-Upon-Tyne (GB)

( * ) Notice: Subject to any disclaimer, the term of this patent is extended or adjusted under 35 U.S.C. 154(b) by 7 days.

(21) Appl. No.: 10/591,312

(22) PCT Filed: Mar. 10, 2005

(86) PCT No.: PCT/GB2005/000921

§ 371 (c)(1),
(2), (4) Date: Sep. 1, 2006

(87) PCT Pub. No.: WO2005/087104

PCT Pub. Date: Sep. 22, 2005

(65) Prior Publication Data

US 2007/0180928 A1      Aug. 9, 2007

(30) Foreign Application Priority Data

Mar. 10, 2004   (GB)   ................... 0405362.5

(51) Int. Cl.
*A61B 5/20* (2006.01)
(52) U.S. Cl. ...................................... 600/573
(58) Field of Classification Search ................. 600/573, 600/574, 576, 584; 73/861, 215
See application file for complete search history.

(56) References Cited

U.S. PATENT DOCUMENTS

| | | | | |
|---|---|---|---|---|
| 3,345,980 A | * | 10/1967 | Coanda | 600/575 |
| 3,871,230 A | * | 3/1975 | Dye et al. | 73/215 |
| 3,871,231 A | | 3/1975 | Ciarico | |
| 4,753,249 A | * | 6/1988 | Muller | 600/584 |
| 4,776,485 A | * | 10/1988 | Brennan | 220/23.83 |
| 5,495,854 A | * | 3/1996 | Currie | 600/573 |

FOREIGN PATENT DOCUMENTS

GB           929181           6/1963

* cited by examiner

*Primary Examiner*—Max Hindenburg
*Assistant Examiner*—Michael C Stout
(74) *Attorney, Agent, or Firm*—MacMillan, Sobanski & Todd, LLC

(57) ABSTRACT

A peak flow measurement device comprises a hollow body (1) having an inlet (8) for receiving fluid and an outlet (3), wherein the inlet (8) and outlet (3) are spaced apart from each other, the cross-sectional area of the body being greater than the cross-sectional area of the outlet and wherein in use the device is oriented such that the inlet is above the outlet and the measured peak flow is proportional to the maximum height (11) of fluid within the body.

20 Claims, 3 Drawing Sheets

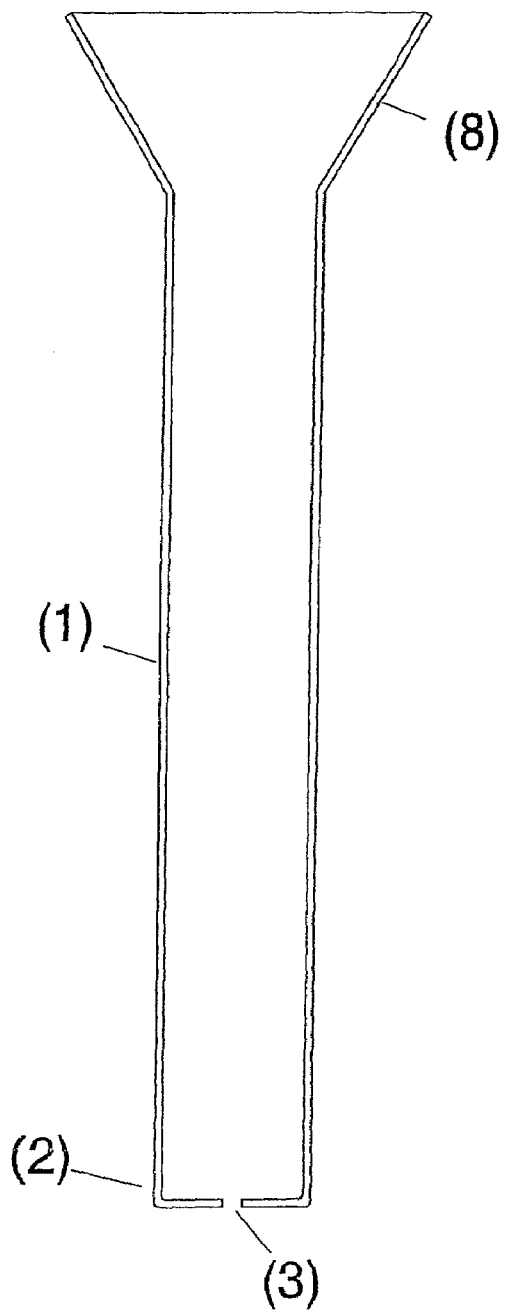
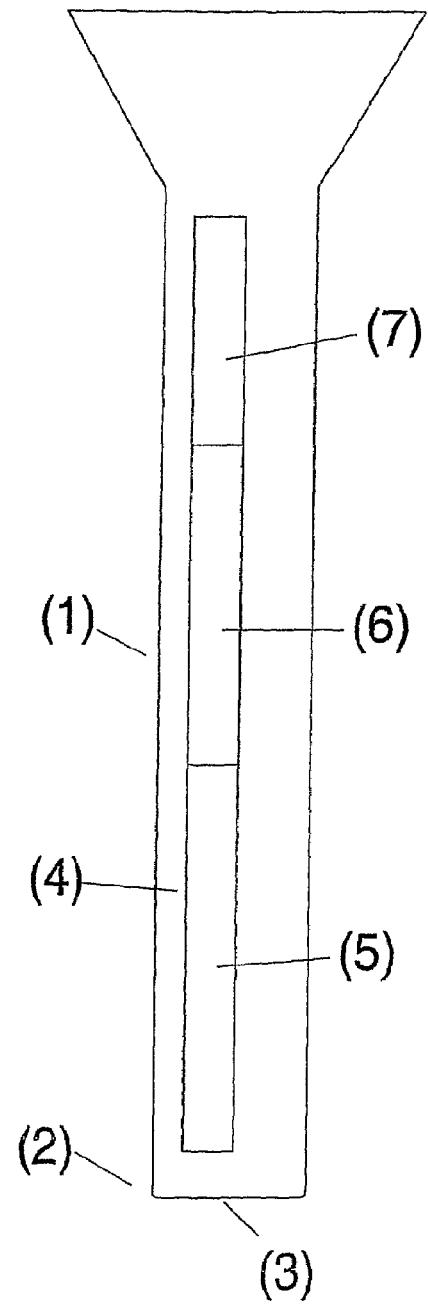
Figure 1
Figure 2

PEAK FLOW MEASUREMENT DEVICE

BACKGROUND OF THE INVENTION

The invention relates to a device to be used for the measurement of the maximum, or peak, rate of urine flow from human subjects, for clinical analytical purposes. Such a measurement is useful as a standard clinical indicator of urodynamic obstruction. The invention could also be adapted as a low cost tool for the gauging of peak fluid flow in other medical and industrial applications.

A constriction or obstruction of the urethra reduces the flow rate of urine. Prostatic hyperplasia is one example of a condition common in males. Urethra damage resulting from trauma is also common, particularly in the case of road accident victims. In general, a peak urine flow rate in excess of 15 milliliters per second is considered normal for a man. A peak flow rate of less than 10 milliliters per second, has a high probability of being associated with an urodynamic obstruction. A measure of peak flow rate therefore provides a useful diagnostic indicator to a physician. Furthermore, the efficacy of treatments for the condition, through surgery, or pharmacological means, may be objectively assessed by measuring urine peak flow rate.

It is desirable to offer a means of peak urine flow measurement that is low cost, does not require the presence of expert staff, and that can preferably be used, unaided, by the patient.

There is a considerable body of prior art in the field. Current use is made of bulky and expensive electronic equipment that measures the peak flow with considerable accuracy, and is often combined with apparatus for retaining the urine sample to allow for laboratory analysis of the urine. Such apparatus requires specially trained staff to operate it, who are required to be present while the urine sample is being provided by the patient. This encroachment on the patient's privacy can interfere with the accuracy of the test result obtained. Other prior art, such as that described in U.S. Pat. No. 4,753,249 represents a variation of a multi-orifice design based on the urinometer of Willard Drake, and as described in his 1953 patent U.S. Pat. No. 2,648,981. By its use of a simple measurement vessel and orifice, the current invention offers a design of significantly reduced complexity and ease of manufacture, appropriate to the rapid screening of patients suffering urodynamic conditions and without recourse to expert assistance.

SUMMARY OF THE INVENTION

The current invention utilises a novel approach to provide a low cost device for the measurement of urine flow in a clinical or home environment. The device may also be adapted for the measurement of liquid flow in other medical or industrial applications where a low cost solution, optionally including that of a disposable one time use device, is appropriate.

One aspect of the invention provides a peak flow measurement device as specified in the claims.

Another aspect of the invention relates to a method of determining the peak flow rate of a fluid as specified in the claims.

Preferred aspects of the invention are specified in the claims dependent on the claims.

The device comprises a vessel formed as a hollow cylinder, solid at one end and open at the other. In use, the cylinder is held vertically, with its solid end downward, and its open end uppermost. A small orifice in the solid end allows liquid within the cylinder to exit at a constricted rate. The open end of the cylinder is available for the introduction of fluid under conditions of non-constricted free flow. The behaviour of fluid progressing through an orifice such as that in the closed end of the cylinder is such that the square of the velocity of the exit stream of fluid is proportional to the height of the fluid in the cylinder. The relationship of the height of the fluid and the orifice radius is determined by the formula, well known in the art of hydrodynamics:

$$\text{Flow Rate} = K \pi r^2 \times \sqrt{(2gh)}$$

Where: K is a constant relating to the configuration of the aperture.

$\pi r^2$ is the area of the aperture.

g is the acceleration due to gravity.

h is the height of fluid in the tube.

Consequently, as fluid is introduced into the cylinder, the height of the fluid will rise initially, and then stabilise at a height at which the efflux through the orifice matches the influx. Provided that the dimensions of the cylinder, and of the orifice, are chosen to be appropriate for the expected total volumetric flow contributing to the measurement, together with the expected flow rates, the maximum height achieved by the fluid in the cylinder will be indicative of the peak influx rate.

The cylinder is preferentially constructed from a transparent material so that either an independent clinician, or the subject him or herself may make note of the height achieved by the fluid during a flow measurement. To assist such measurement, the outer surface of the cylinder may include an engraved or printed scale of a complexity appropriate to the application. In one embodiment of the invention, a simple scale consisting of three coloured bars is used. For the measurement of urine flow in men, a coloured bar would extend from the dosed end of the cylinder to the height at which a flow of 10 milliliters per second was appropriate. A differently coloured bar would extend from the height at which a flow of 10 milliliters per second was appropriate to the height at which a flow of 15 milliliters per second was appropriate. A third bar of a third colour would extend beyond this. An optional addition to the scale would be the inclusion of a strip of a suitable heat sensitive material extending the full length of the cylinder, such that the height gained by a warm fluid in the cylinder could be rendered more apparent to the observer.

The open end of the cylinder may preferentially be connected to a flared receptacle or funnel to assist the introduction of the fluid into the cylinder.

BRIEF DESCRIPTION OF THE DRAWINGS

FIG. 1 is a sectional elevational view of a first embodiment of a peak flow measurement device in accordance with this invention.

FIG. 2 is an elevational view of the first embodiment of the peak flow measurement device illustrated in FIG. 1.

DETAILED DESCRIPTION OF THE PREFERRED EMBODIMENTS

Figure 3:
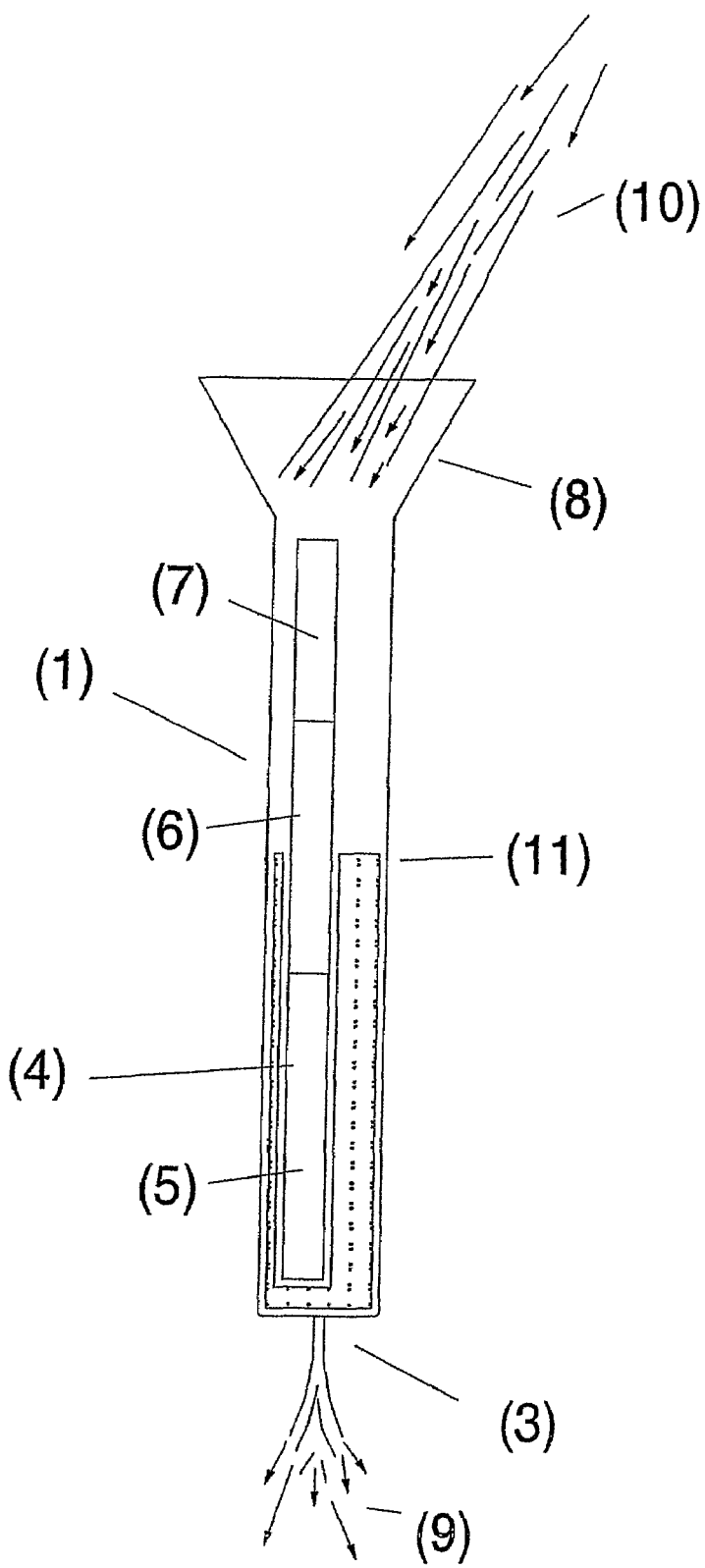
FIG. 3 is an elevational view similar to FIG. 2 showing the first embodiment of the peak flow measurement device during use.

One embodiment of the invention will now be described by way of example, with reference to the attached diagrams. FIG. 1 shows a schematic cross section through the device, which, in this embodiment, is manufactured using vacuum formed plastics, or similar techniques. The cylinder (1) is of 30 mm internal diameter, and 200 mm in length. The closed end of the cylinder (2) is perforated by an orifice (3), of 4 mm diameter. The upper end of the cylinder is flared to form a catchment funnel (8).

FIG. 2 shows an external view of the cylinder. The external surface of the cylinder has affixed a printed label (4), extending the length of the tube, and approximately 10 mm wide. The label is coloured red in its lower section (5), yellow in its mid section (6), and green in the upper section (7). The boundary between the red (5) and yellow (6) sections corresponds with a fluid height in the cylinder appropriate to that achieve with a sustained flow of 10 ml per second of fluid introduced to the cylinder. The boundary between the yellow (6), and green (7), sections corresponds with a fluid height in the cylinder appropriate to that achieve with a sustained flow of 15 ml per second of fluid introduced to the cylinder.

FIG. 3 shows the device in use. In order to measure a patient's peak urine flow, the cylinder is held vertically over a lavatory bowl so that the fluid (9) emerging from the orifice (3) may conveniently be disposed of. Alternatively, a receptacle can be provided if an analysis of the fluid is subsequently required. The patient then directs his urine (10) into the open end of the cylinder through the catchment funnel (8). As the stream of urine enters the cylinder (1), the level of the urine in it rises until the efflux balances the influx of urine, at which point the level (11) remains constant. Ultimately, as the patient's urine flow is exhausted, the level drops, until the device is once again empty. An attendant, or the patient himself, observes the highest level (11) achieved in the cylinder, and notes whether this corresponds with the red (5), yellow (6), or green (7), section of the label (4).

Other colours, and a greater or lesser number of sections may be used where it is considered appropriate. In-another similar embodiment, the label's coloured sections are replaced with numbered sections. In a further embodiment for use in pediatrics, smaller dimensions may be adopted for the cylinder and the orifice, and the coloured label is replaced with one which has cartoon characters, or the like, to identify the three sections.

In another embodiment, a strip of liquid crystal or similar heat sensitive indicating film is applied, either independently, or alongside the label. As urine is expelled from the body at an elevated temperature, the cylinder wall will heat up where immersed. By choosing a suitable transition temperature, and a non-reversible type of indicator, a permanent indication of the achieved urine flow may be presented. In a further refinement, the strip is placed on an area of the cylinder whose wall thickness has been reduced in order to maximise the heat transfer.

In yet another embodiment, the internal diameter of the cylinder may be varied along its length in order to provide a greater accuracy of measurement at certain specific measured flow rates of interest.

Figure 4:
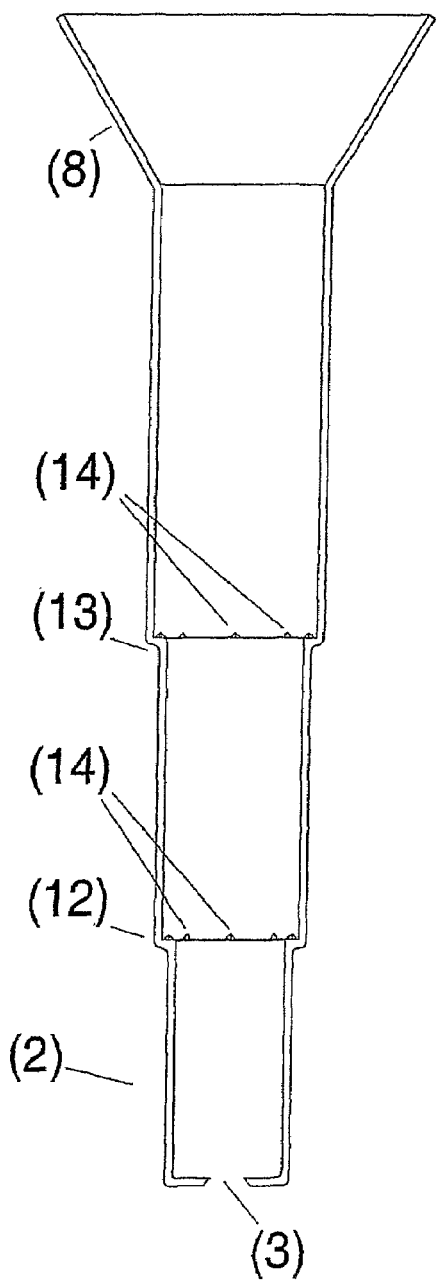
FIG. 4 is a sectional elevational view of a second embodiment of a peak flow measurement device in accordance with this invention.
Figure 5:
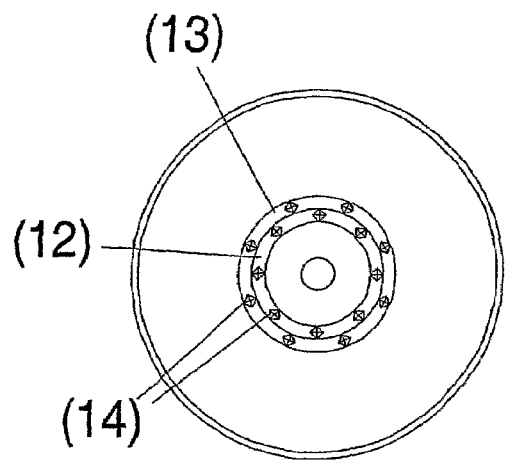
FIG. 5a is a top plan view showing the second embodiment of the peak flow measurement device illustrated in FIG. 4 in a first stage of use.
FIG. 5b is a top plan view showing the second embodiment of the peak flow measurement device illustrated in FIG. 4 in a second stage of use.
FIG. 5c is a top plan view showing the second embodiment of the peak flow measurement device illustrated in FIG. 4 in a third stage of use.
Figure 5:
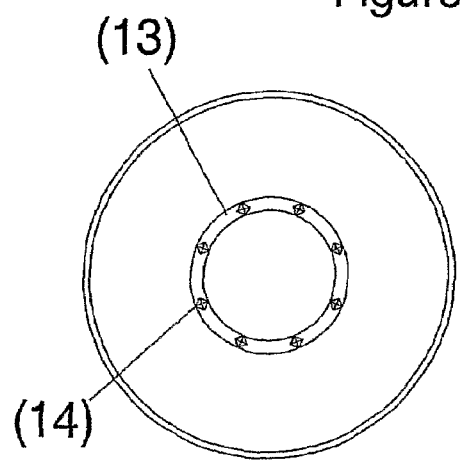
Figure 5:
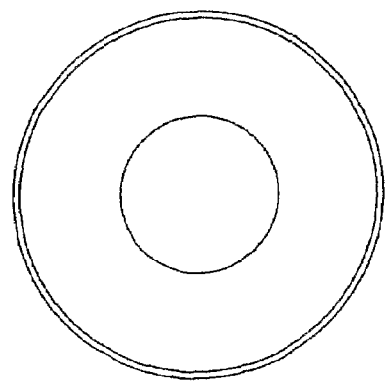

A further embodiment is shown in FIG. 4 which shows the diameter of the cylinder increasing step-wise, at specific measurement heights that relate to significant flow rates. When a subject looks vertically downwards into the cylinder, as might a test subject when urinating into it, concentric rings will thus be observed at the shoulder of each step. As each step shoulder is immersed in urine, the subject may easily assess whether the height achieved by the urine surpasses the step. In the diagram of FIG. 4, an orifice (3) of diameter 4.6 mm perforates the solid end of the hollow cylindrical vessel (2), having an internal diameter of 16 mm. The orifice is bevelled, such that its diameter increases through the thickness of the solid end of the vessel resulting in a hydro-dynamically thin orifice being presented to the fluid efflux. At a height of 36 mm above the orifice (12) the diameter of the vessel expands to 20 mm, arid at a further height of 46 mm, (13) it expands again to 24 mm. These heights are chosen such that they correspond to efflux flow rates at the orifice of 10 ml per second and 15 ml per second respectively. Above the second step the vessel extends further, to a catchment funnel (8). FIG. 5a shows the view into the vessel from above, as seen by the subject when the level in the vessel is below the first shoulder step. FIG. 5b shows the same view but with urine filling the tube to a level between the two steps, and FIG. 5c shows the same view with a level surpassing both shoulder steps. To further enhance the visibility of the step, a series of pyramidal teeth (14) may optionally be incorporated into the rim of the step, which, under lateral illumination, renders even 125 better visibility of their state of immersion in urine, to the observer.

The invention claimed is

1. A fluid flow measurement device comprising:
   a hollow body having an inlet for receiving fluid and an outlet that defines a flow rate of fluid therethrough, wherein:
   the inlet and outlet are spaced apart from each other,
   the cross-sectional area of the body is greater than the cross-sectional area of the outlet,
   in use, the device is oriented such that the inlet is above the outlet and the measured fluid flow is proportional to the height of fluid within the body,
   the hollow body comprises at least two portions having different cross sectional areas, and
   the cross sectional area of the hollow body increases step-wise at a height on the body that relates to a predetermined flow rate of fluid through the outlet.

2. A device as claimed in claim 1, wherein the outlet is circular in cross-section.

3. A device as claimed in claim 1, wherein the outlet is so shaped and dimensioned as to present a hydro-dynamically thin orifice to fluid efflux.

4. A device as claimed in claim 1, further comprising scale means for determining the peak height of fluid in the hollow body.

5. A device as claimed in claim 4, wherein the scale means comprises at least one indicia.

6. A device as claimed in claim 4, wherein the scale means comprises at least two different coloured bars each representing a different peak flow rate or range of peak flow rates.

7. A device as claimed in claim 4, wherein the scale means comprises heat sensitive material providing a semi-permanent or permanent indication of fluid height.

8. A device as claimed in claim 7, wherein the heat sensitive material is applied to a wall of the hollow body.

9. A device as claimed in claim 8, wherein the heat sensitive material is applied to a portion of the wall of the hollow body with reduced wall thickness.

10. A device as claimed in claim 1, wherein the hollow body is constructed from a transparent material.

11. A device as claimed in claim 1, wherein the inlet is connectable to a funnel.

12. A device as claimed in claim 1, wherein the hollow body is cylindrical in shape.

13. A device as claimed in claim 12, wherein the hollow body has a diameter of 30 mm and the outlet orifice has a diameter of 4 mm.

14. A device as claimed in claim 1, wherein scale means for determining the peak height of fluid passing through the hollow body comprises the step-wise changes in the cross-sectional area of the hollow body.

15. A device as claimed in claim 1, wherein each step-wise increase in the cross-sectional area of the hollow body includes a step, and wherein at least one pyramidal tooth is incorporated into the rim of each step.

16. A device as claimed in claim 1, wherein the fluid is urine.

17. A device as claimed in claim 1 further comprising a receptacle for catching effluxed fluid.

18. A device as claimed in claim 1, wherein each step-wise increase in the cross-sectional area of the hollow body includes a step, and wherein each step extends perpendicularly relative to a wall of the hollow body.

19. A device as claimed in claim 1, wherein each step-wise increase in the cross-sectional area of the hollow body includes a step, and wherein a plurality of pyramidal teeth is incorporated into the rim of each step.

20. A method for determining the peak flow rate of a fluid using the device as claimed in claim 1, comprising the steps of
(a) introducing fluid to the inlet of the device; and
(b) determining the peak fluid level within the hollow body;
wherein the peak fluid flow rate is proportional to the maximum height of fluid in the body.

* * * * *